Figure 1:
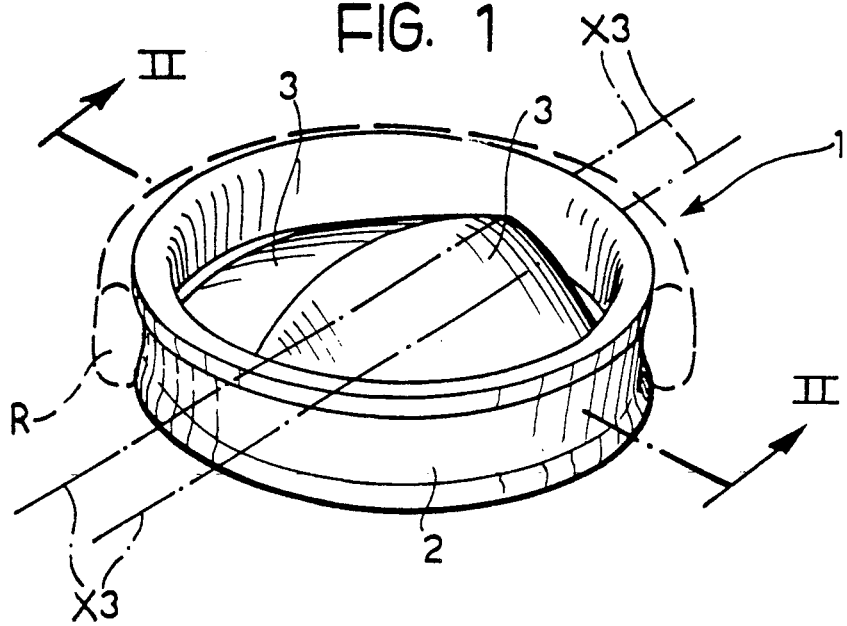

United States Patent [19]
Bona et al.

[11] Patent Number: 5,002,567
[45] Date of Patent: Mar. 26, 1991

[54] PROSTHETIC HEART VALVE

[75] Inventors: Gioachino Bona, Turin; Stefano Rinaldi, Parma; Franco Vallana, Turin, all of Italy

[73] Assignee: Sorin Biomedica S.p.A., Saluggia, Italy

[21] Appl. No.: 278,273

[22] Filed: Nov. 30, 1988

[30] Foreign Application Priority Data

Jan. 12, 1988 [IT] Italy .................. 67010 A/88

[51] Int. Cl.$^5$ .............................................. A61F 2/24
[52] U.S. Cl. ...................... 623/2; 137/512.1; 137/527
[58] Field of Search ............... 623/2; 137/527, 512.1

[56] References Cited

U.S. PATENT DOCUMENTS

| | | | |
|---|---|---|---|
| 3,513,485 | 5/1970 | Davila | 623/2 |
| 3,824,629 | 7/1974 | Shiley | 623/2 |
| 4,021,863 | 5/1977 | Woien | 137/527 |
| 4,274,437 | 6/1981 | Watts | 623/2 |
| 4,689,046 | 8/1987 | Bokros | 623/2 |
| 4,808,180 | 2/1989 | Johnson | 623/2 |
| 4,822,353 | 4/1989 | Bokros | 623/2 |

FOREIGN PATENT DOCUMENTS

| | | | |
|---|---|---|---|
| 0050439 | 10/1981 | European Pat. Off. | |
| 0176337 | 9/1985 | European Pat. Off. | |
| 0207594 | 1/1987 | European Pat. Off. | 623/2 |
| 0211576 | 2/1987 | European Pat. Off. | 623/2 |

Primary Examiner—Randall L. Green
Assistant Examiner—Stephanie L. Iantorno
Attorney, Agent, or Firm—Hedman, Gibson, Costigan & Hoare

[57] ABSTRACT

In a prosthetic heart valve comprising a generally annular stent and at least two obturators mounted in the stent so as to be above to pivot between an open position and a closed position, the stent is provided with at least one element which projects inwardly of the stent itself, while each of the obturators has recesses which cooperate with the projecting element of the stent with clearance in a generally-hinged configuration which enables the obturators to pivot between the open position and the closed position.

7 Claims, 2 Drawing Sheets

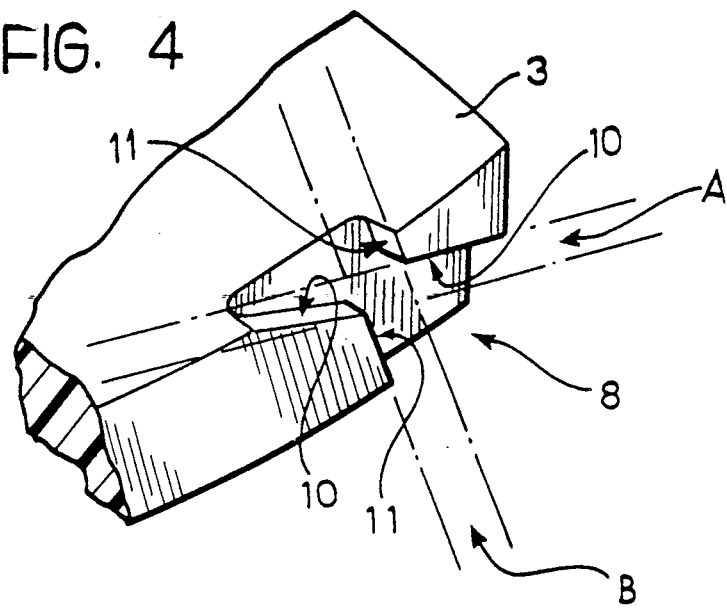
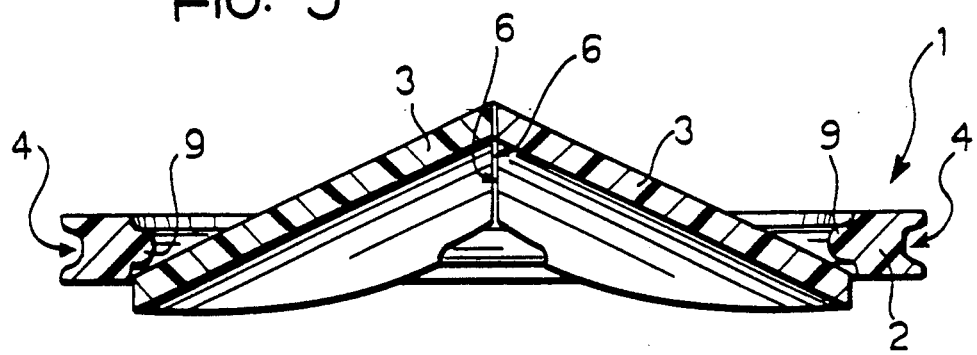
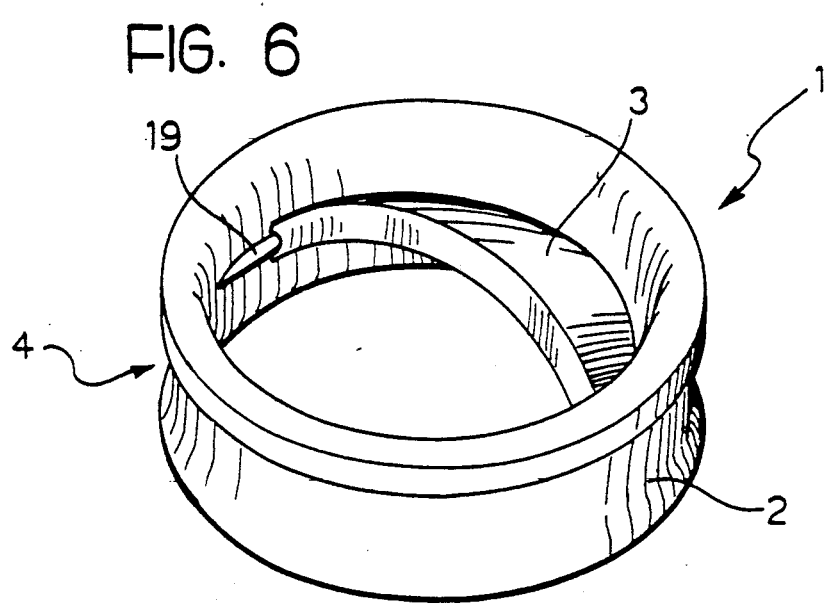

PROSTHETIC HEART VALVE

The present invention relates to prosthetic heart valves and particularly to a prosthetic heart valve comprising a generally-annular stent intended to be traversed by the blood and at least two obturators mounted in the stent so as to be able to pivot between an open position, in which the obturators allow the blood to pass freely through the stent in a first direction, and a closed position, in which the obturators jointly prevent the blood from passing through the stent in the direction opposite the first direction.

Prosthetic heart valves of the type specified above, which are usually provided with two obturators, are widely known in the art and are currently known as "bi-leaflet" or double semi-disc valves.

Generally, in known prosthetic heart valves with several obturators, the pivoting of the obturators is achieved by the provision thereon of projecting formations which engage like pins in corresponding recesses provided in the wall of the orifice of the valve stent.

A solution of this type is described, for example, in Italian patent application No. 67815-A/86 in the name of the same Applicants.

Experiments and clinical tests carried out with known valves show that, whilst their performance can be considered generally satisfactory, they are still far from perfect from several points of view.

For example, the articulation of the obturators by means of pins which cooperate with recesses provided in the stent of the prosthesis causes the fraction of blood which passes over the articulation zone, causing the so-called washing of the articulation itself, to follow a path which is removed or diverted from the main flow of blood through the prosthesis.

Another possible disadvantage lies in the fact that the cross-section of the prosthesis stent usually has to be increased in the zones in which the recesses for engaging the pins of the obturator are situated, and forms a thickening (or shoulder) which reduces the cross-section available for the passage of blood through the prosthesis. There are usually two thickenings or shoulders of this type in a prosthesis including two obturators and this can reduce the useful cross-section for the blood flow significantly.

Moreover, the region immediately downstream of the shoulders (in the direction of flow of the blood through the prosthesis) may constitute a region in which the blood is relatively stagnant and in which thrombogenic phenomena can arise more easily.

Finally, in known solutions, the axes about which the obturators pivot, which are identified by the pins of the obturators and by the corresponding recesses provided in the stent, are in fixed positions. This means that the obturators continue to orient about the same axes throughout the entire useful life of the prosthesis.

This means that certain parts of the prosthesis, and always the same parts, are subject to marked strain and are therefore potentially subject to wear and breakage. Moreover, the positions of the pivot axes of the obturators are decided univocally by the position in which the prosthesis is implanted, which is selected once and for all by the surgeon during implantation. It is, however, possible that the optimum position of the prosthesis from the point of view of its operation will vary with time.

The object of the present invention is to provide a prosthetic heart valve of the type specified above, which is improved particularly as regards:

the possibility of having a larger useful cross-section for the passage of blood through the prosthesis, the elimination of potential zones of stagnation of the blood, and the possibility of enabling the obturators to orient or rotate relative to the stent of the prosthesis.

According to the present invention, this object is achieved by virtue of a prosthetic heart valve of the type specified above, characterised in that:

the stent has at least one element which projects inwardly of the stent itself, and each of the obturators has recesses which cooperate with clearance with the at least one projecting element in a hinged configuration, enabling the obturator to pivot between the open position and the closed position.

Figure 2:
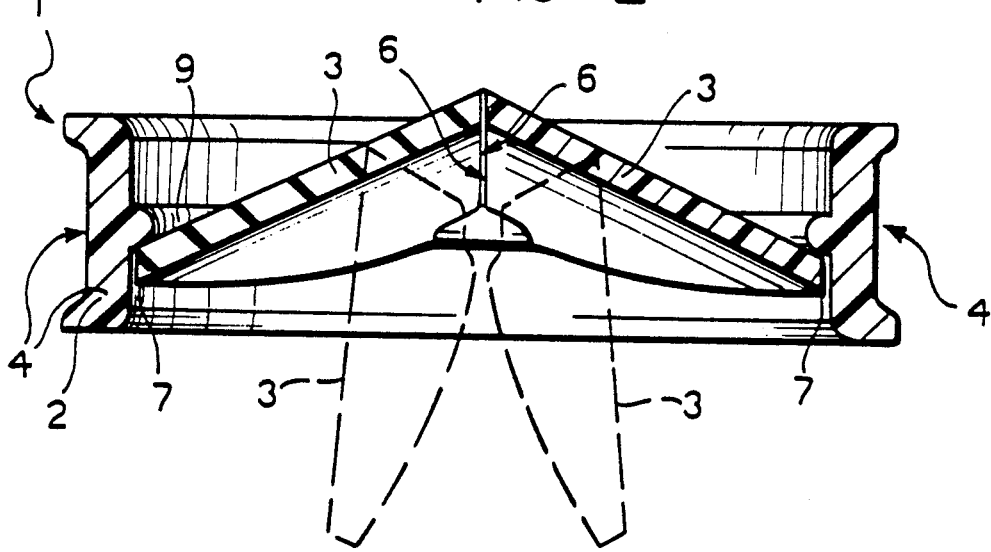
Figure 3:
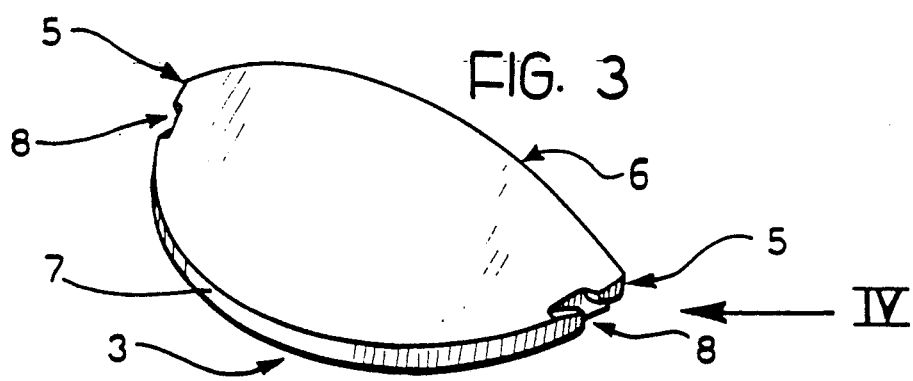

The invention will now be described, purely by way of non-limiting example, with reference to the appended drawings, in which:

FIG. 1 is a perspective view of a prosthetic heart valve according to the invention, FIG. 2 is a cross-section taken on the line II—II of FIG. 1, on an enlarged scale, FIG. 3 is a perspective view of one of the elements illustrated in FIGS. 1 and 2, FIG. 4 is a view on an enlarged scale, of the part of FIG. 3 indicated by the arrow IV, FIG. 5 is a cross-section corresponding substantially to the cross-section of FIG. 2, showing a first possible variant of the prosthetic valve according to the invention, and FIG. 6 is a perspective view of another possible embodiment of the prosthetic valve according to the invention.

In the drawings, a prosthetic heart valve intended to be used to replace a natural heart valve (for example the aortic valve or the mitral valve) which has suffered as a result of cardiac valve damage or of cardiopathy, is generally indicated 1.

In accordance with a widely-known solution, the prosthesis 1 comprises:

a generally annular-shaped stent which defines within it a passage for the blood, and a plurality of obturators (usually two) indicated 3 of generally eyelid or nail shape.

The obturators 3 are mounted within the stent 2 so as to be pivotable between a closed position (shown in continuous outline in FIG. 2) and an open position (shown in broken outline, also in FIG. 2). For the purposes of the present description, it may be assumed that this pivoting takes place about respective lines approximately identifiable by the axes $X_3$ (see FIG. 1).

In their open position, the obturators 3 extend in positions almost perpendicular to the general plane of the stent 2 and thus enable the blood to flow freely through the prosthesis in a first direction (downwards with reference to the orientation of FIG. 2).

When the direction of the blood flow is reversed by the action of the heart muscle, the blood pressure itself automatically causes the obturators 3 to move into their closed position in which the obturators 3 jointly occlude the orifice of the prosthesis, preventing the blood from flowing in the opposite direction (upwards with reference to the orientation of FIG. 2).

The stent 2 is made from a rigid material, for example metal or a pyrolitic carbonaceous material, or a combination of the two (metal core covered with carbonaceous material, or carbonaceous material with a metal reinforcing structure).

The stent 2 usually has a groove 4 in its outer surface for facilitating the assembly of a suture ring around the stent 2 which enables the prosthesis to be fixed to the annulus of the natural valve after its valve flaps have been removed The cross-section of the suture ring R, which is made of a woven textile made from biocompatible thread (for example threads of the materials known commercially as Dacron ® and Teflon ®) is illustrated schematically in broken outline in FIG. 1 only.

The obturators 3 may be constituted by a core (for example of graphite), covered with a layer of biocompatible carbonaceous material deposited by high-temperature pyrolisis (pyrocarbon) or by cathode spraying (sputtering). Alternatively the obturators 3 may be made entirely of carbonaceous material Similar layers of biocompatible carbonaceous material may also be applied to the stent 2 and to the suture ring R, at least in the parts which will be exposed to the blood flow.

The oburators 3 are generally eyelid-shaped (see FIG. 3); each is seen to have two opposing vertices 5, between which extend the inner side 6 of the obturator (which will cooperate with the corresponding side of the other obturator in the closed position—FIGS. 2 and 5) and the outer side 7 of the same obturator (which will cooperate with the wall of the valve orifice in the closed position).

The salient characteristic of the prosthetic valve according to the invention is that each obturator 3 has respective recesses 8 near its vertices 5 for cooperation with projecting elements (protuberances) 9 provided on the wall of the orifice of the prosthesis.

The obturators 3 are mounted in the stent 2 so that the portions in which the recesses 8 are provided are arranged, so as to speak, astride the annular projection 9. In order to achieve this result, the obturators 8 may, in general, be arranged adjacent their final positions of assembly and then pressed slightly to cause their deformation and consequent snap-engagement with the projection 9. Alternatively, the same result can be achieved by action on the stent 2 (for example by its resilient deformation).

In the embodiments to which FIGS. 1 to 5 relate, the projection 9 is constituted by an annular body of semicircular cross-section which projects from the inner wall of the stent 2 around its entire circumference. The projection 9 thus has two sides which face in opposite directions, towards the two axial ends of the stent 2 respectively.

As can better be seen in the enlarged view of FIG. 4, the recesses 8 are generally butterfly-shaped. Each recess 8 is thus seen to have two pairs of "diagonally opposite" sides 10, 11.

The dimensions of the recesses 8 are such as to achieve a hinged engagement with the projection 9, with sufficient clearance to enable the obturators 3 to pivot freely about the axes $X_3$ between their closed positions and their open positions.

The relative positions and inclinations of the diagonally opposite sides or faces 10, 11 of the recesses are selected so that:

the sides 10 are brought into contact with opposite sides (in an axial direction) of the projection 9 when each obturator 3 is in its closed position (relative position indicated A in FIG. 4), and the other two sides 11 are brought into contact with the opposite sides of the projection 9 when the obturators are in their open positions (relative position indicated B in FIG. 4).

The amplitude of the movement of the obturators 3 in pivoting between their open positions and their closed positions can therefore be determined univocally by the selection of corresponding inclinations of the sides or faces 10 and 11 of the recesses 8.

The same end positions of the pivoting movement of the obturators 3 may, however, also be determined by other means, for example by means of abutments provided on the stent 2, or, particularly in the case of the closed position, by the shaping of the outer side 7 of each obturator 3 so that this side abuts the corresponding wall of the annular projection 9 precisely when the obturator 3 reaches the closed position.

With the use of this solution in particular, the height of the stent 2 (that is, its axial extent in the direction of the blood flow) may be reduced to a minimum, in practice corresponding to the axial extent of the projection 9. This solution is shown schematically in FIG. 5 which shows a prosthesis in which the stent 2 is practically reduced to a ring with a very small height, much less than the axial bulk (that is in the direction of the blood flow of the obturators 3 in their closed position.

This variant is particularly advantageous in terms of the reduction of the overall bulk of the prosthesis 1 and also as regards any traumatic effects which could be caused in that region of the annulus where the prosthesis 1 is sutured if the stent 2 were of excessive axial length.

In the embodiments illustrated in FIGS. 1 to 5 it is implicitly assumed that the projecting element or protuberance 9 provided within the stent 2 extends continuously around the entire circumference of the stent 2, that is around the entire periphery of the prosthesis.

This solution is particularly advantageous since it enables the obturators to rotate freely about the main axis of the stent 2 so that the angular positions of the respective pivot axes $X_3$ relative to the stent itself vary.

The engagement between the recesses 8 and the projections 9 does in fact have sufficient clearance to enable the obturators to rotate around the periphery of the stent 2. Naturally this orienting movement does not cause the obturators 3 to be released from the stent 2 because of the mutual restraining action which the obturators 3 exert on each other.

As stated above, the ability of the obturators 3 to rotate (with the change in the angular position of the pivot axes $X_3$ relative to the stent 2) has the advantage that it prevents certain operating forces from being applied constantly to the same region of the stent 2 and thus achieves a uniform distribution of the wear.

In order to facilitate the orienting action, it is possible to provide the obturators 3 with a configuration, or shape, which is "fluidodynamically-asymmetric" relative to the blood flow duct defined by the stent 2. In other words, the obturators 3 may be provided (naturally in a concordant manner for the two obturators 3) with a generally asymmetric configuration similar to that of a propellor blade. This shaping operation (whose result is not obviously visible in the appended drawing for reasons of scale) can easily be achieved during the shaping of the graphite cores of the obturators 3, which are usually produced by cutting from a lump of graphite by means of numerically-controlled tools.

By virtue of their generally blade-like configuration, when the obturators 3 are impinged upon by the blood flow (particularly at the beginning of the opening phase, that is when the direction of the blood flow is reversed and impinges on the extradotal faces—that is the convex face—of the obturators 3) the obturators tend to rotate slightly relative to the general plane of the prosthesis 1, with a slight angular displacement of the respective axes $X_3$ relative to the stent 2, as well as pivoting about these same axes $X_3$ towards the open position.

The ability of the obturators 3 to rotate freely relative to the main axis of the prosthesis 1 is also advantageous since it enables the obturators 3 themselves to orient automatically into the position of least resistance to the blood flow, and thus to assume spontaneously the most effective position from the point of view of the operation of the prosthesis.

The substantial advantages of the invention are, however, retained even when the projecting element provided on the inner surface of the stent 2 does not extend around the entire periphery of the prosthesis, but only in correspondence with two diametrally opposite portions.

This solution is illustrated schematically in FIG. 6, which shows a prosthesis 1 in which one of the obturators 3 has been removed to show the presence of a protuberance 19 which projects from the inner surface of the stent 2 and cooperates in a generally hinged configuration with the recesses 8 provided at the ends 5 of the obturators 6.

In general terms, the projecting elements 19 of FIG. 6 (only one is properly visible in the drawing) are approximately comparable to two diametrally opposite pieces of the continuous element 9 illustrated in the other figures.

In general, the solution illustrated in FIG. 6 does not provide the possibility of the obturators 3 rotating relative to the stent 2, but does retain the advantage resulting from the larger free cross-section for the passage of the blood and other advantages inherent in the washing action of the hinge zones of the obturators 3 by the blood.

Naturally, the principle of the invention remaining the same, the details of construction and forms of embodiment may be varied widely with respect to those described and illustrated without thereby departing from the scope of the present invention.

What is claimed is:

1. A prosthetic heart valve comprising a generally annular stent intended to be traversed by the blood in use and at least two obturators mounted in said stent so as to be able to pivot between an open position in which they allow the blood to pass freely through said stent in a first direction, and a closed position, in which they jointly prevent the blood from passing through said stent in the direction opposite said first direction, wherein:

said stent has at least one element which projects inwardly from the stent of the valve of a sufficient length along the inside diameter of the stent for pivoting of the obturators to their open and closed positions responsive to the flow of blood, each of said obturators includes recesses which cooperate with at least said one projecting element of said stent with clearance in a generally-hinged configuration to enable the pivoting of said obturator and for enabling the blood flow to converge towards the interior of the valve when said obturators impinge against at least said one projecting element of said stent, and wherein each of said obturators is generally eyelid-shaped with two opposite vertices and an outer edge extending between said two opposite vertices and each of said recesses in said obturators cooperates with at least said one projecting element of said stent in such a way that said outer edge is brought into abutment with said cooperating projecting element when the obturator is in said closed position.

2. A prosthetic valve according to claim 1, wherein each said projecting element has opposite faces and each said recess is generally butterfly-shaped and defined by diagonally-opposite pairs of sides; said sides of said pairs being able to cooperate with said opposite faces of a said projecting element to define at least one of said open and closed positions of said obturators.

3. A prosthetic valve according to claim 1, wherein each said obturator includes two of said recesses each provided near one of said two vertices.

4. A prosthetic valve according to claim 1, wherein at least said one projecting element has a dimension axial to said stent and said stent has an axial dimension substantially corresponding with said dimension of at least said one projective element.

5. A prosthetic valve according to claim 1, including two said obturators.

6. A prothetic valve according to claim 1, wherein said projecting element is in the form of an annular protuberance extending around the entire circumference of said stent so that said obturators can rotate relative to said stent to vary the angular positions of their pivot axes relative to said stent.

7. A prothetic valve according to claim 6, wherein said obturators have fluidodynamically-asymmetric shapes with respect to the duct for the blood flow defined by said stent, so that the blood flow in the duct can cause the obturators to rotate relative to the stent so as to vary said angular positions of their pivot axes.

* * * * *